United States Patent [19]

Umeda

[11] Patent Number: 4,841,951
[45] Date of Patent: Jun. 27, 1989

[54] ANGLE PORTION OF ENCOSCOPE

[76] Inventor: Hiroyuki Umeda, c/o Machida Endoscope Co., Ltd., 13-8, Honkomagome 6-chome, Bunkyo-ku, Tokyo, Japan

[21] Appl. No.: 237,500

[22] Filed: Aug. 26, 1988

[30] Foreign Application Priority Data

Aug. 28, 1987 [JP] Japan .......................... 62-131098[U]

[51] Int. Cl.⁴ ............................................. A61B 1/00
[52] U.S. Cl. .................................................... 128/4
[58] Field of Search ...................... 128/4, 6; 138/120

[56] References Cited

U.S. PATENT DOCUMENTS 3,799,151  3/1974  Fukaumi et al. .......................... 128/6
4,773,395  9/1988  Suzuki et al. ............................ 128/4

Primary Examiner—William H. Grieb
Attorney, Agent, or Firm—Peter L. Berger

[57] ABSTRACT

An angle portion of an endoscope comprising a flexible tube having a polydirectional distal tip. A series of four-directional rings are arranged to form the rear part of the angle portion, a series of two-directional rings are subsequently arranged to form the front part of the angle portion, and the distal tip is connected to the top end of the front part of the angle portion.

1 Claim, 2 Drawing Sheets

PRIOR ART

ANGLE PORTION OF ENCOSCOPE

BACKGROUND OF THE INVENTION

The present invention relates to a structure of an angle portion of an endoscope.

FIG. 3 is an entire side view of an industrial or medical endoscope. The conventional technique will now be described with reference to FIG. 4, which is a side view illustrating the main part of the endoscope.

In the drawings, reference numeral 1 represents a flexible tube, reference numeral 2 represents a handle and reference numeral 3 represents a conduit, and the endoscope is constructed so that the flexible tube is inserted into the body to be observed and the interior of the body is observed.

More specifically, a distal tip 4 is located on the top end of the flexible tube 1, and an observing window, an illuminating window, an air-jetting and water-jetting opening, a sucking opening, a forceps opening and tope ends of various articles to be introduced according to need are arranged in the rigid tip end portion 4. Reference numeral 5 represents an angle portion continuous to this rigid top end portion 4 and comprises continuous rings arranged so that the posture of the distal tip 4 is changed in up-and-down and left-and-right four directions, as described hereinafter. The present device relates to this angle portion.

The handle 2 comprises operating knobs 6a and 6b for changing the direction of the distal tip 4, and the operating knobs 6a and 6b are arranged so that an operating wire passed through the interior of the flexible tube 1 is operated by the knobs 6a and 6b to change the direction of the distal tip 4. Reference numeral 7 represents an eyepiece portion, and an image guide or C.C.D. is laid out between the eyepiece portion and the observing window.

A light guide for guiding light to the illuminating window, an air and water feed pipe and a sucking pipe are arranged within the conduit 3 so that these members can be connected to a light source and a pump.

In the above-explained endoscope, the angle portion 5 comprises rings 8a and 8b connected to each other and tunably arranged at positions different by 90° as shown in FIG. 4 and a cover capped on the periphery, and these rings of the angle portion are arranged to that the operating wire not shown in the drawings is operated by the operating knobs 6a and 6b of the handle 2 to turn the distal tip 4 in the desired direction among the up-and-down and the left-and-right directions, as pointed out hereinbefore.

According to the above-mentioned conventional technique, for example, when the inlet of the stomach is observed, the angle portion is caused to make a U-turn for the observation. Namely, the angle portion is turned upward and the posture is changed in the left-and-right direction.

In this case, the posture of the observing window of the distal tip 4 is not changed in the left-and-right direction as shown in FIG. 6 and only the upwardly bent part is moved in the left-and-right direction as shown in FIG. 5, and the observing window of the distal tip 4 is directed to the center and the flexible tube is located in the central portion of the visual field.

Also, since the connecting part between the distal tip 4 and the angle portion 5 also acts as a connecting part for the article to be introduced, bending of this connecting part is rendered difficult by the resistance of the article. Since the operating wire is operated to forcible change the direction of the connecting part, heavy loads are imposed on the article introduced and the operating wire, resulting in degradation of the durability.

SUMMARY OF THE INVENTION

In accordance with the present invention, there is provided an angle portion in which the front part may not follow the bending with the rear part when it is bent to the left and right direction. In this novel structure, the central axis of the front part of the angle portion is controlable to come off from the central axis of the flexible tube.

More specifically, in accordance with the present invention, there is provided an endoscope comprising a flexible tube having a distal tip and an angle portion, a hadle having a knob for operating an angle-operating wire and a conduit for guiding an article to be introduced, in which an angle portion is bendable in up-and-down and left-and-right four directions, the present divice relates to the angle portion, which is characterized in that a series of four-directional rings are arranged to form the rear part of the angle portion, a series of two-directional rings are subsequently arranged to form the front part of the angle portion, and the distal tip is connected to the top end of the front part of the angle portion.

In the above-mentioned structure, in the case where it is intended to change the observing direction of the observing window of the distal tip to the left-and-right direction in the state where the angle portion is caused to make a U-turn upward(downward), by bending the angle portion to the direction opposite to the desired direction to produce a diagonal state, bending starts immediately from the connecting part between the flexible tube and the angle portion, the connecting part of the four-direction rings is greatly distorted and bent by about 90° to the side opposite to the desired direction, and the distal tip is diagonally turned in the desired direction.

It is a primary object of the present invention to provide an angle portion in which the observing direction of the observing window of the distal tip can be turned to the left or right while it is bent upward (downward).

Another object of the present invention is to provide an angle portion which can operate the U-turn observation of, for example, the inlet of the stomach.

Still another object of the present invention is to provide an angle portion which can face the observing window to the U-turn-viewing objective of the desired direction without force, and improve the durability in the angle-operating wire and the article to be introduced, such as an image guide or a light guide, and an effect of facilitating control and maintenance can be attained.

DETAILED DESCRIPTION OF THE PREFERRED EMBODIMENTS

One embodiment of the present device will now be described with reference to the accompanying drawings.

Figure 1:
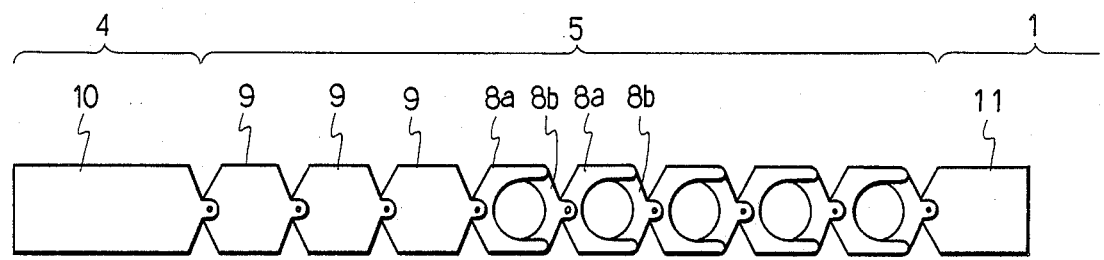
FIG. 1 is a side view showing a main part of one embodiment of the present device.

FIG. 1 is a side view illustrating the state of rings of the angle portion. In FIG. 1, four-directional rings 8a and 8b are turnably arranged and connected at positions different by 90° so that the rings can be bent in up-and-down and left-and-right four directions over a predetermined width.

Two-directional rings 9 are turnably connected over a predetermined width to the tope end of the series of four-directional rings 8a and 8b so that the rings 9 are not bent in left-and-right directions but are bent only in up-and-down two directions. The angle portion 4 is thus constructed by combining the rear part consisting of the four-directional rings 8a and 8b with the front part consisting of the two-directional rings 9. Reference numeral 10 represents a cylinder of the distal tip 4, and referential numeral 11 represents a rear end connecting ring.

Figure 2:
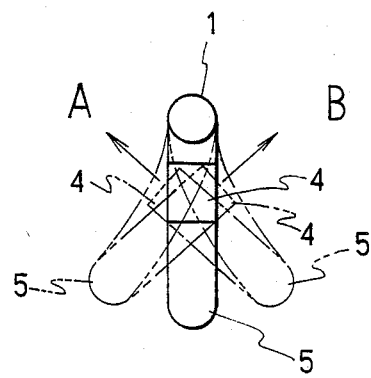
FIG. 2 is a front view showing the bent state of an angle portion.
Figure 3:
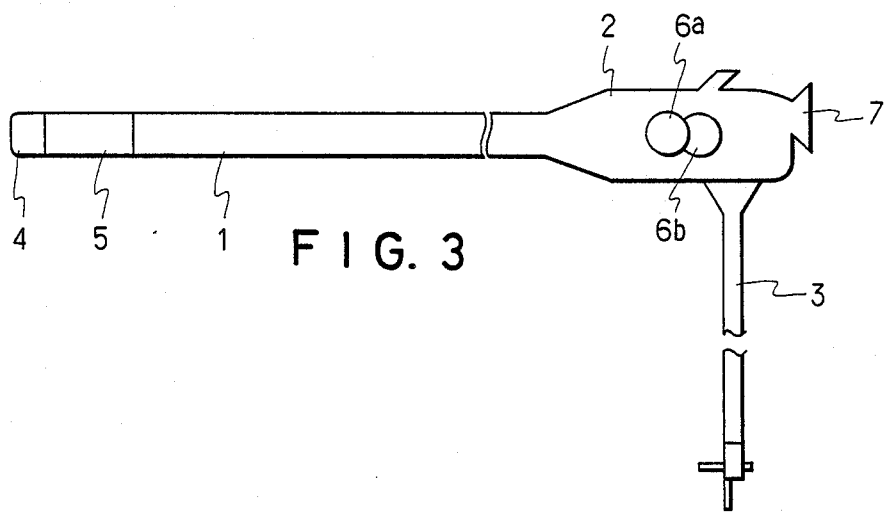
FIG. 3 is a side view of an endoscope.
Figure 4:
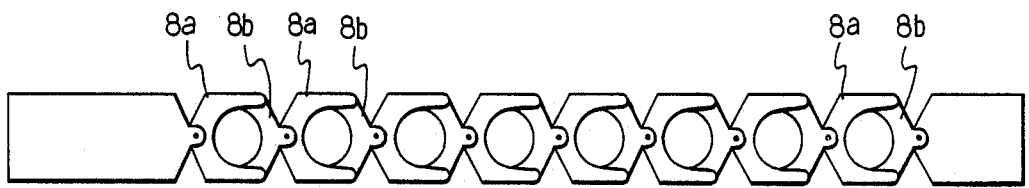
FIG. 4 is a side view showing a main part of the conventional technique.
Figure 5:
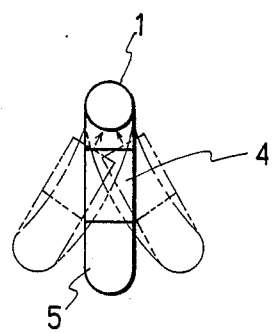
FIG. 5 is a front view showing the bent state in the conventional technique.
Figure 6:
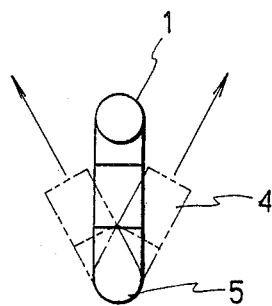
FIG. 6 is a front view showing an ideal bent state.

In the above-mentioned structure, in the case where it is intended to change the direction of the distal tip 4 to the left or right in the state where the angle portion 5 is bent upward (downward), an operator controls the angle portion 5 to bend in the direction opposite to the desired direction. For example, as shown in FIG. 2, if the U-turn-viewing objective exists on the A side of the flexible tube 1, the angle portion 5 is bent into the B side. On the other hand, if the U-turn-viewing objective exists on the B side of the flexible tube 1, the angle portion 5 is bent into the A side.

By this control, as shown in FIG. 2, the rear part of the angle portion 5 which comprises a series of four-directional rings 8a, 8b is bent into the left or right direction. At this moment, the central axis of the rear part of the angle portion 5 is on the central axis of the flexible tube 1.

However, the front part of the angle portion 5 may not follow this bending of left or right direction, because it comprises a series of two-directional rings 9 which do not allow the front part to bend into the left or right direction.

Therefore, the central axis of the front part is twisted and come off from the central axis of the flexible tube 1 so that the observing window of the distal tip 4 faces diagonally to the U-turn-viewing objective of the desired direction. At this moment, because the central axis of the front part of the angle portion 5 is out of the central axis of the flexible tube 1, the flexible tube 1 is beyond the range of the observing window.

Accordingly, the observing window face to the U-turn-viewing objective without force.

In this manner, the U-turn-viewing objective, for example, the inlet of the stomach, is observed.

What is claimed is:

1. In an endoscope comprising a flexible tube having a distal tip and an angle portion, a handle having a knob for operating an angle-operating wire and a conduit for guiding an article to be introduced, in which an angle portion is bendable in up-and-down and left-and-right four directions, the angle portion characterized in that a series of four-directional rings are arranged to form the rear part of the angle portion, a series of two-directional rings are subsequently arranged to from the front part of the angle portion, and the distal tip is connected to the top end of the front part of the angle portion.

* * * * *